US007932273B2

(12) United States Patent
Schmid et al.

(10) Patent No.: US 7,932,273 B2
(45) Date of Patent: Apr. 26, 2011

(54) 3-[(2-{[4-(HEXYLOXYCARBONYLAMINO-IMINOMETHYL) PHENYLAMINO]METHYL}-1-METHYL-1H-BENZIMIDAZOL-5-CARBONYL)PYRIDIN-2-YLAMINO] PROPIONIC ACID ETHYLESTER METHANSULFONATE AND ITS USE AS A MEDICAMENT

(75) Inventors: Rolf Schmid, Baltringen (DE); Peter Sieger, Mittelbiberach (DE); Rainer Sobotta, Ingelheim am Rhein (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 390 days.

(21) Appl. No.: 12/022,655

(22) Filed: Jan. 30, 2008

(65) Prior Publication Data
US 2008/0119523 A1 May 22, 2008

Related U.S. Application Data

(63) Continuation of application No. 10/918,017, filed on Aug. 13, 2004, now abandoned.

(60) Provisional application No. 60/503,316, filed on Sep. 16, 2003.

(30) Foreign Application Priority Data

Aug. 29, 2003 (DE) .................................. 103 39 862

(51) Int. Cl.
  *A61K 31/4439* (2006.01)
  *C07D 401/12* (2006.01)
(52) U.S. Cl. ..................................... 514/338; 546/273.4
(58) Field of Classification Search ............... 546/273.4; 514/338
See application file for complete search history.

(56) References Cited

U.S. PATENT DOCUMENTS

| | | | |
|---|---|---|---|
| 4,367,217 A | 1/1983 | Gruber et al. | |
| 4,427,648 A | 1/1984 | Brickl et al. | |
| 4,438,091 A | 3/1984 | Gruber et al. | |
| 4,675,405 A | 6/1987 | Musser et al. | |
| 5,416,099 A | 5/1995 | Hartman et al. | |
| 5,434,150 A | 7/1995 | Austel et al. | |
| 5,800,836 A | 9/1998 | Morella et al. | |
| 6,087,380 A | 7/2000 | Hauel et al. | |
| 6,414,008 B1 | 7/2002 | Hauel et al. | |
| 6,469,039 B1 | 10/2002 | Hauel et al. | |
| 6,627,646 B2 * | 9/2003 | Bakale et al. | 514/322 |
| 6,710,055 B2 | 3/2004 | Hauel et al. | |
| 6,900,229 B2 | 5/2005 | Hauel et al. | |
| 7,189,743 B2 | 3/2007 | Hauel et al. | |
| 7,202,368 B2 | 4/2007 | Zerban et al. | |
| 2003/0181488 A1 | 9/2003 | Brauns | |
| 2005/0038077 A1 | 2/2005 | Kohlrausch et al. | |
| 2005/0095293 A1 | 5/2005 | Brauns et al. | |
| 2005/0107438 A1 | 5/2005 | Radtke et al. | |
| 2006/0183779 A1 | 8/2006 | Brauns | |
| 2006/0222640 A1 | 10/2006 | Reilly et al. | |
| 2006/0247278 A1 | 11/2006 | Sieger et al. | |
| 2006/0276513 A1 | 12/2006 | Hauel et al. | |
| 2007/0105753 A1 | 5/2007 | Eisert et al. | |
| 2007/0149589 A1 | 6/2007 | Zerban et al. | |
| 2007/0185173 A1 | 8/2007 | Zerban et al. | |
| 2007/0185333 A1 | 8/2007 | Zerban et al. | |

FOREIGN PATENT DOCUMENTS

| | | |
|---|---|---|
| DE | 19752843 A1 | 7/1999 |
| DE | 10245624 A1 | 4/2004 |
| EP | 0540051 A1 | 5/1993 |
| EP | 0623596 A1 | 11/1994 |
| EP | 0655439 A2 | 5/1995 |
| JP | 58134033 | 8/1983 |
| WO | 9837075 | 8/1998 |
| WO | 03/007984 | 1/2003 |

OTHER PUBLICATIONS

Doelker, english translation of Ann. Pharm. Fr. 2002, 60:161-176, pp. 1-39.*

Singhal et al., "Drug Polymorphism, etc.," Advanced drug delivery reviews 56, 335-347 (2004).*

CMU Pharmaceutical polymorphism, Internet p. 1-3 (2002) (print out Apr. 3, 2008).*

Davidovich, M., et al Detectio of Polymorphism by Powder X-Ray Diffraction: Interference by Preferred Orientation; American Pharmaceutical Review. IN: Russell Pub., 2004, 7(1) pp. 10, 12, 14, 16, and 100.

Ciara, Mino R.; Crystalline Polymorphism of Organic Compounds; Topics in Current Chemistry, 198, Berlin Heidelberg: Springer Vertag, 1998 pp. 164-208.

Berstein, Joel; Polymorphism in Molecular Crystals; Oxford: Clarendon Press, 2002, pp. 117, 118, 272 and 273.

Doelker; English Translation of S.T.P., Pharma Pratiques (1999), 9(5), 399-409, pp. 133.

Ulicky, L. and Kemp, T.J.; Comprehensive Dictionary of Physical Chemistry; NY: PTR Prentice Hall (1992) p. 21.

Haleblian, John and McCrone Walter; Pharmaceutical Applications of Polymorphism; Journal of Pharmaceutical Sciences, (1969), 58 pages 911-929.

Chemical & Engineering News, Feb. 2003, pp. 32-35.

Brittain, Harry G.; Polymorphism in Pharmaceutical Solids; NY: Marcel Dekker, Inc, 1999, pp. 1-2, 188-226.

US Pharmacopia #23, National Formulary #18 (1995) pp. 1843-1844.

(Continued)

*Primary Examiner* — Patricia L Morris
(74) *Attorney, Agent, or Firm* — Michael P. Morris; Wendy A. Petka

(57) ABSTRACT

Ethyl 3-[(2-{[4-(hexyloxycarbonylaminoiminomethyl)phenylamino]methyl}-1-methyl-1H-benzimidazole-5-carbonyl) pyridin-2-ylamino]propionate methanesulfonate in the crystalline modifications I and II and as the hemihydrate and the use thereof as a pharmaceutical composition.

2 Claims, 4 Drawing Sheets

OTHER PUBLICATIONS

Muzaffar, N.A., et al: Polymorphism and Drug Availability, Journal of Pharmacy (Lahore) 1979, 1(1), 59-66.

Jain, N. K. and Mohammed, M.N.; Polymorphism, Indian Drugs, 1986, 23 (6), pp. 316-329.

Taday, P.F., et al; Using Terahertz Pulse Spectroscopy to Study the Crystalline Structure of a Drug: A Case Study of the Polymorphs of Ranitidine Hydrochloride; Journal of Pharmaceutical Sciences, 92 (4), 2003, pp. 831-838.

Wall, G. Michael; Pharmaceutical applications of Drug Crystal Studies; Pharmaceutical Manufacturing, 1986, pp. 33-42.

Concise Encyclopedia, NY: Walter de Gruyter, 1994, pp. 872-873.

Otuska, M., et al: Effect of Polymorphic Forms of Bulk Powders on Pharmaceutical Properties of Carbamazepine Granules; Chem. Pharm. Bull. 47(6)0, pp. 852-856 (1999).

Hauel, N.H., Structure-Based Design of Novel Potent Nonpeptide Thrombin Inhibitors, J. Med. Chem. 2002, 45, 1757-1766, XP 001098844.

Nagahara, T., et al; Dbasic (Amidinoaryl) Propanoic Acid Derivatives as Novel Blood Coagulation Factor Xa Inhibitors, J. Med. ,Chem. 1994, 37, pp. 1200-1207.

Mungall, Dennis, BIBR-1048 Boehringer Ingelheim, Current Opinion in Investigational Drugs, 2002 3(6) 905-907-XP001147306.

Stangier, et al; Abstract of J Thrombosis and Haemotosis, vol. I, Supplement 1, Jul. 12-18, 2003.

Gustafsson<D., Abstract of J. Intern. Med. Oct. 2003 254(4); 322-34: PMID: 12974871.

Stangier, et al; Abstract of the J. of Clinical Pharmacology, 2005; 45: 555-563.

The Merck Index 14th Edition, Merck & Co., NJ, USA, 2001, No. 9156, 4308 and 845, Ecuador, (Dec. 2006).

Berge, Stephen M., et al; Pharmaceutical Salts; Journal of Pharmaceutical Sciences (1977) vol. 66, No. 1 pp. 1-19.

Collins, Ben, et al; Antithrombotic Drug Market; Nature Review: Drug Discovery (2003) vol. 2, No. 1, pp. 11-12.

Stangier, J., et al; Pharmacokinetics of BIBR 953 W, A Novel Low molecular Weight Direct Thrombin Inhibitor in Healthy Volunteers; Supplement to the Journal Thrombosis and Haemostasis (2001) Abstract.

* cited by examiner

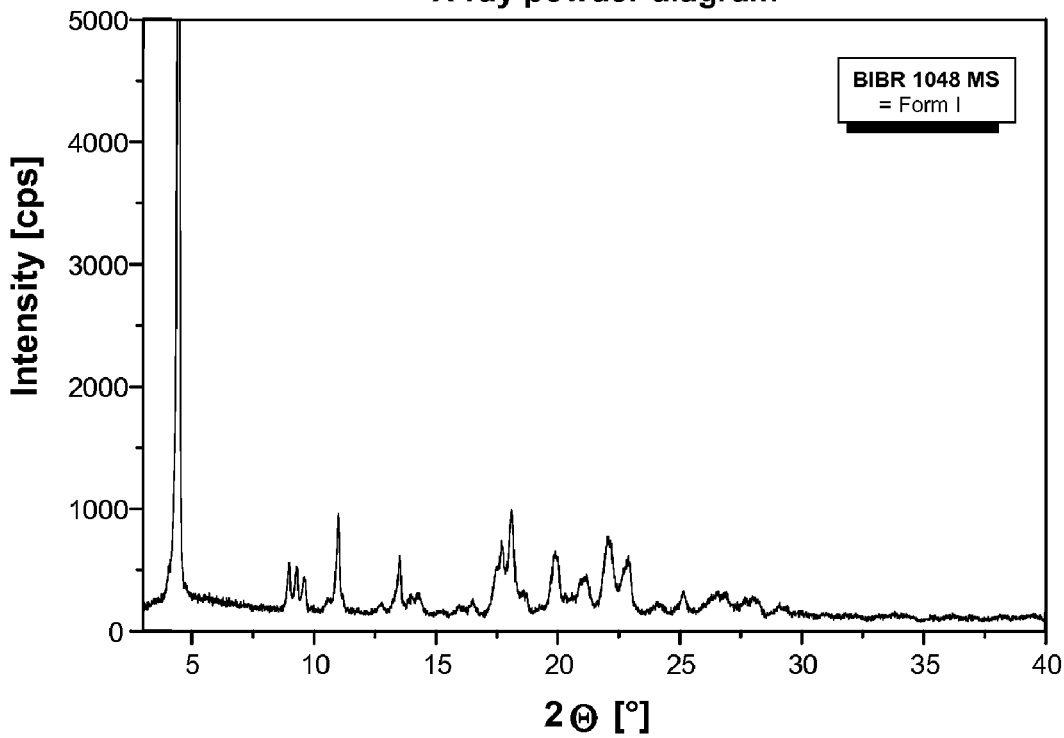
FIG. 1
X-ray powder diagram
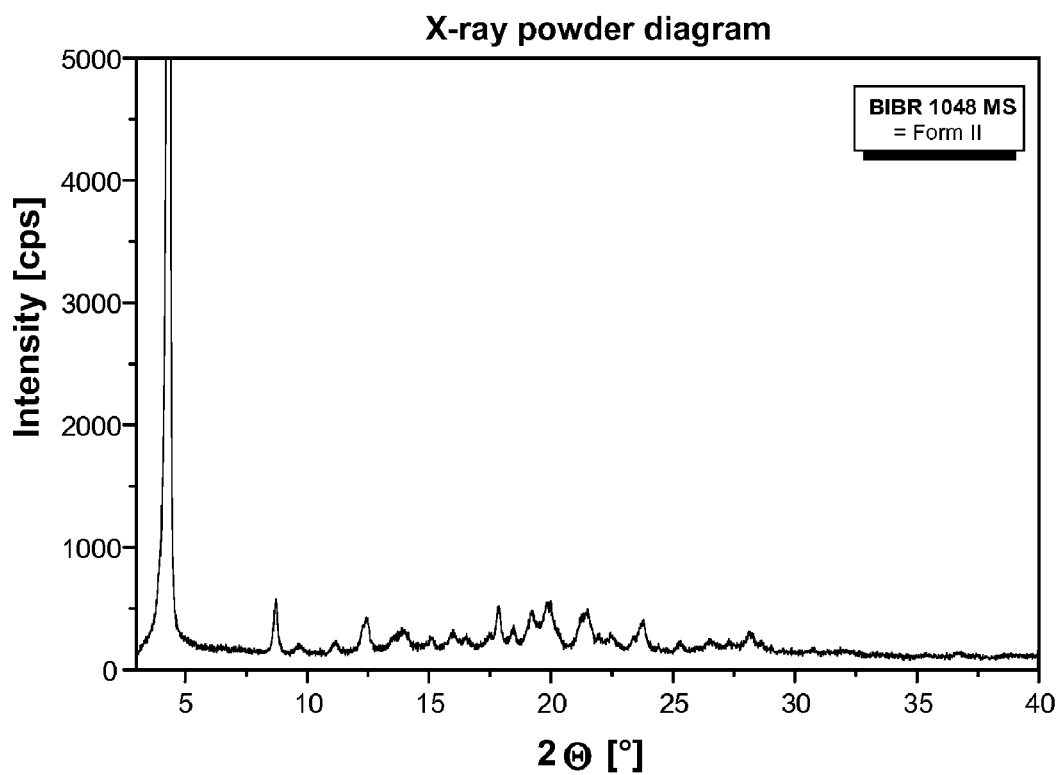
X-ray powder diagram

DSC - Diagram of the hemihydrate of BIBR 1048 MS

3-[(2-{[4-(HEXYLOXYCARBONYLAMINO-IMINOMETHYL) PHENYLAMINO]METHYL}-1-METHYL-1H-BENZIMIDAZOL-5-CARBONYL)PYRIDIN-2-YLAMINO] PROPIONIC ACID ETHYLESTER METHANSULFONATE AND ITS USE AS A MEDICAMENT

RELATED APPLICATIONS

This application is a continuation of co-pending application Ser. No. 10/918,017, filed Aug. 13, 2004, which claims benefit of U.S. Ser. No. 60/503,316, filed Sep. 16, 2003, and claims priority to German Application No. DE 103 39 862.7, filed Aug. 29, 2003, each of which is hereby incorporated by reference in its entirety.

FIELD OF THE INVENTION

The present invention relates to the compound ethyl 3-[(2-{[4-(hexyloxycarbonylaminoimino-methyl)phenylamino] methyl}-1-methyl-1H-benzimidazole-5-carbonyl)pyridin-2-ylamino]propionate methanesulfonate of formula A and the use thereof as a pharmaceutical composition.

application of the compound of chemical formula A are the post-operative prophylaxis of deep vein thrombosis and the prevention of stroke.

The abovementioned pharmacologically beneficial properties of the disubstituted bicyclic heterocycles disclosed in the prior art are the main prerequisite for effective use of the compounds as pharmaceutical compositions. An active substance must, however, also meet other requirements in order to be capable of being used as pharmaceutical compositions. These parameters are to a large extent connected with the physicochemical nature of the active substance.

Without being restricted thereto, examples of these parameters are the stability of effect of the starting substance under different ambient conditions, stability in the course of the preparation of the pharmaceutical formulation, and stability in the final compositions of the pharmaceutical preparation. The pharmaceutical active substance used to prepare the pharmaceutical compositions should therefore have high stability, which should also be guaranteed even under different environmental conditions. This is absolutely essential to prevent the use of pharmaceutical compositions which contain, in addition to the active substance itself, breakdown products thereof, for example. In such cases the content of active substance found in the pharmaceutical formulations might be less than specified.

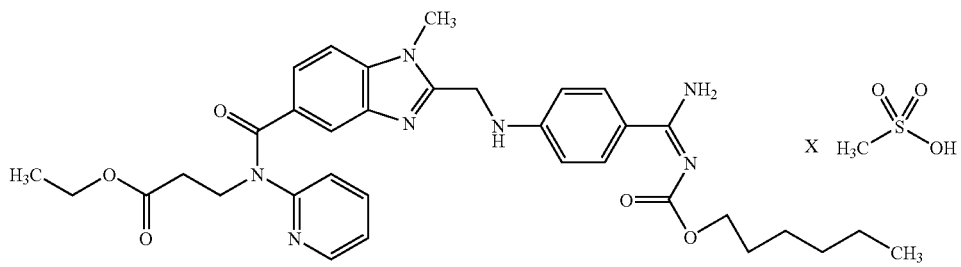

Formula A

The base of the compound of formula A is already known from WO 98/37075, in which compounds with a thrombin-inhibiting effect and a thrombin time-prolonging activity are disclosed, under the name 1-methyl-2-[N-[4-(N-n-hexyloxy-carbonylamidino)phenyl]-aminomethyl]benzimidazol-5-yl-carboxylic acid-N-(2-pyridyl)-N-(2-ethoxycarbonylethyl)-amide. The compound of formula I is a double prodrug of the compound of formula B

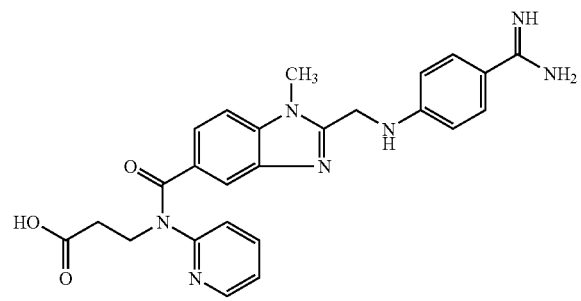

Formula B i.e., the compound of formula A (BIBR 1048 MS) is only converted into the actual effective compound, namely the compound of formula B, in the body. The main fields of The absorption of moisture reduces the content of pharmaceutically active substance as a result of the increased weight caused by the uptake of water. Pharmaceutical compositions with a tendency to absorb moisture have to be protected from moisture during storage, e.g., by the addition of suitable drying agents or by storing the drug in an environment where it is protected from moisture. In addition, the uptake of moisture may reduce the content of pharmaceutically active substance during manufacture if the pharmaceutical substance is exposed to the environment without being protected from moisture in any way. Preferably, therefore, a pharmaceutically active substance should be only slightly hygroscopic.

As the crystal modification of an active substance is important to the reproducible active substance content of a preparation, there is a need to clarify as far as possible any existing polymorphism of an active substance present in crystalline form. If there are different polymorphic modifications of an active substance, care must be taken to ensure that the crystalline modification of the substance does not change in the pharmaceutical preparation later produced from it. Otherwise, this could have a harmful effect on the reproducible potency of the drug. Against this background, active substances characterized by only slight polymorphism are preferred.

Another criterion which may be of exceptional importance under certain circumstances, depending on the choice of formulation or the choice of manufacturing process, is the solubility of the active substance. If, for example, pharmaceutical solutions are prepared (e.g., for infusions), it is essential that the active substance should be sufficiently soluble in physiologically acceptable solvents. It is also very important for drugs which are to be taken orally that the active substance should be sufficiently soluble.

The problem of the present invention is to provide a pharmaceutically active substance which not only is characterized by high pharmacological potency but also satisfies the above-mentioned physicochemical requirements as far as possible.

DETAILED DESCRIPTION OF THE INVENTION

Figure 1:
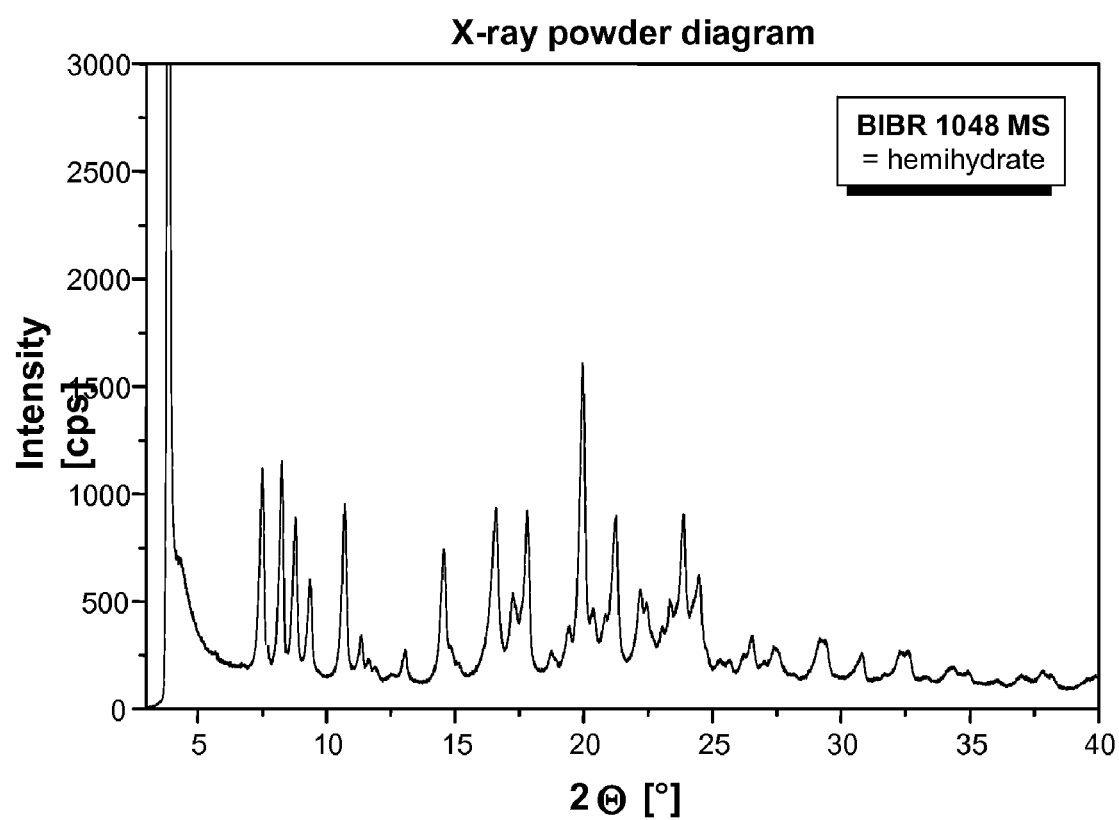
FIG. 1 shows the X-ray powder diffractograms of the three crystalline forms of ethyl 3-[(2-{[4-(hexyloxycarbonylaminoiminomethyl)phenylamino]methyl}-1-methyl-1H-benzimidazole-5-carbonyl)pyridin-2-ylamino]propionate methanesulfonate.

The problem outlined above is solved by the ethyl 3-[(2-{[4-(hexyloxycarbonylaminoiminomethyl)phenylamino]methyl}-1-methyl-1H-benzimidazole-5-carbonyl)pyridin-2-ylamino]propionate methanesulfonate salt of formula A.

In fact, it has been found, surprisingly, that crystalline modification I of this salt can be prepared by the process described in Example 1 and crystalline modification II of this salt can be prepared by the processes described in Examples 2 to 4, selectively and uniformly in each case.

Moreover, under certain conditions of synthesis as described, for example, in Example 5, a hydrate form may be obtained, the water content of which indicates a hemihydrate.

For use of the pharmaceutical composition, it is essential that the active substance contained therein is in a uniform crystalline modification to ensure reliable bioavailability.

The methanesulfonate according to the invention is characterized in all three crystalline modifications by good crystallinity and low amorphization during grinding and compression. Moreover, it is non-hygroscopic in all three crystalline modifications and dissolves very easily in physiologically acceptable acid aqueous media.

The crystalline forms of the methanesulfonate of the compound ethyl 3-[(2-{[4-(hexyloxycarbonylaminoiminomethyl)phenylamino]methyl}-1-methyl-1H-benzimidazole-5-carbonyl)pyridin-2-ylamino]propionate according to the invention are characterized by a melting point of $T_{mp}=180°$ C.$\pm 3°$ C. (form I), $T_{mp}=190°$ C.$\pm 3°$ C. (form II), or $T_{mp}=120°$ C.$\pm 5°$ C. (hemihydrate) (determined by DSC=Differential Scanning Calorimetry; evaluation by peak maximum; heating rate: 10° C./min). The values shown were determined using a DSC 821$^e$ made by Messrs. Mettler Toledo.

In a first aspect, the present invention therefore relates to the three above-mentioned polymorphic forms of the salt ethyl 3-[(2-{[4-(hexyloxycarbonylaminoiminomethyl)phenylamino]methyl}-1-methyl-1H-benzimidazole-5-carbonyl)pyridin-2-ylamino]propionate methanesulfonate, preferably in crystalline form, characterized by melting points of $T_{mp}=180°$ C.$\pm 3°$ C., $T_{mp}=190°$ C.$\pm 3°$ C. or $T_{mp}=120°$ C.$\pm 5°$ C. (determined by DSC; evaluation by peak maximum; heating rate: 10° C./min). Polymorph I with a melting point of $T_{mp}=180°$ C.$\pm 3°$ C. is preferred.

The invention also relates to the methods of selectively producing the three polymorphic forms as well as the modifications which may be obtained by these methods. According to the invention, BIBR 1048 MS polymorph I is obtained by:
  (a) slowly adding a solution of a slight deficiency (for example, 0.98 equivalents) of methanesulfonic acid in acetone to a solution of BIBR 1048 base in acetone at a temperature of approximately 30° C. to 36° C.;
  (b) stirring the mixture for about 1 hour at a temperature of approximately 26° C. to 33° C.;
  (c) cooling the mixture to approximately 17° C. to 23° C. and stirring for a further 40 to 80 minutes at this temperature;
  (d) suction filtering the precipitated crystals of BIBR 1048 MS form I; and
  (e) drying the product thus obtained in vacuo for at least 4 hours at a maximum temperature of 50° C.

According to the invention, BIBR 1048 MS polymorph II is obtained by:
  (a) slowly adding a solution of a slight deficiency (for example, 0.98 equivalents) of methanesulfonic acid in acetone to a solution of BIBR 1048 base in acetone at a temperature of approximately 40° C. to 46° C.;
  (b) optionally inoculating the mixture with BIBR 1048 polymorph II crystals;
  (c) stirring the mixture for about 1 hour at a temperature of approximately 40° C. to 46° C.;
  (d) cooling the mixture to approximately 17° C. to 23° C. and stirring for a further 40 to 80 minutes at this temperature;
  (e) suction filtering the precipitated crystals of BIBR 1048 MS form II; and
  (f) drying the product thus obtained in vacuo for at least 4 hours at a maximum temperature of 50° C.;
or by
  (a) heating a suspension of BIBR 1048 MS polymorph I in acetone to 45° C. to 50° C. for approximately 4 hours with stirring;
  (b) optionally (i) inoculating the mixture with BIBR 1048 polymorph II crystals, or (ii) inoculating the mixture with BIBR 1048 polymorph II crystals and additionally adding a small amount of BIBR 1048 base;
  (c) cooling the mixture to approximately 15° C.;
  (d) suction filtering the precipitated crystals of BIBR 1048 MS form II; and
  (e) drying the product thus obtained in vacuo for at least 4 hours at a maximum temperature of 50° C.;
or by
  (a) placing BIBR 1048 MS polymorph I in acetone;
  (b) optionally (i) inoculating the mixture with a small amount of BIBR 1048 polymorph II, or (ii) inoculating the mixture with BIBR 1048 polymorph II crystals and additionally adding a small amount of BIBR 1048 base;
  (c) heating the mixture thus obtained to 40° C. to 46° C. for at least one hour with stirring;
  (d) cooling the mixture to approximately 17° C. to 23° C. and stirring for a further 40 to 80 minutes at this temperature;
  (e) separating off the precipitated crystals of BIBR 1048 MS form II; and
  (f) drying the product thus obtained in vacuo for at least 4 hours at a maximum temperature of 50° C.

According to the invention, BIBR 1048 MS hemihydrate is obtained by:
  (a) slowly adding a solution of one equivalent of methanesulfonic acid in ethyl acetate to a solution of BIBR 1048 base in a mixture of 90% aqueous ethanol and ethyl acetate in a ratio by volume of approximately 2:5 at a temperature of approximately 35° C. to 40° C.;

(b) optionally adding more ethyl acetate as a diluent at the start of the crystallization of the product;

(c) stirring the mixture for approximately another 30 minutes at approximately 35° C. to 40° C.;

(d) stirring the mixture for a further 30 minutes at ambient room temperature;

(e) suction filtering the precipitate of BIBR 1048 MS hemihydrate; and (f) drying the precipitate at approximately 40° C. in a circulating air drying cupboard.

The crystalline forms of ethyl 3-[(2-{[4-(hexyloxycarbonylaminoiminomethyl)phenylamino]-methyl}-1-methyl-1H-benzimidazole-5-carbonyl)pyridin-2-ylamino]propionate methanesulfonate according to the invention were investigated in more detail by X-ray powder diffraction. The diagrams obtained are shown in FIG. 1. Tables 1 to 3 that follow list the data obtained in this analysis.

TABLE 1

X-ray powder reflections and intensities (standardized) of ethyl 3-[(2-{[4-(hexyloxycarbonylaminoiminomethyl)phenylamino]methyl}-1-methyl-1H-benzimidazole-5-carbonyl)pyridin-2-ylamino]propionate methanesulfonate (form I)

| 2Θ [°] | $d_{hkl}$ value [Å] | intensity [%] |
|---|---|---|
| 4.4 | 20.1 | 100 |
| 8.94 | 9.90 | 5 |
| 9.23 | 9.57 | 4 |
| 9.55 | 9.26 | 4 |
| 10.55 | 8.38 | 2 |
| 10.95 | 8.08 | 11 |
| 12.73 | 6.95 | 1 |
| 13.46 | 6.57 | 7 |
| 13.95 | 6.34 | 3 |
| 14.26 | 6.21 | 2 |
| 15.17 | 5.84 | 1 |
| 15.93 | 5.56 | 1 |
| 16.46 | 5.38 | 1 |
| 17.66 | 5.02 | 8 |
| 18.07 | 4.91 | 13 |
| 18.60 | 4.77 | 2 |
| 19.89 | 4.46 | 6 |
| 20.28 | 4.38 | 2 |
| 20.54 | 4.32 | 2 |
| 21.12 | 4.20 | 4 |
| 22.06 | 4.03 | 8 |
| 22.85 | 3.89 | 6 |
| 24.12 | 3.69 | 1 |
| 25.10 | 3.54 | 3 |
| 25.99 | 3.43 | 1 |
| 26.52 | 3.36 | 2 |
| 26.83 | 3.32 | 2 |
| 27.16 | 3.28 | 1 |
| 27.64 | 3.22 | 2 |
| 28.09 | 3.17 | 2 |
| 29.08 | 3.07 | 1 |
| 29.26 | 3.05 | 1 |
| 29.94 | 2.98 | 1 |
| 31.88 | 2.80 | 1 |
| 34.37 | 2.61 | 1 |
| 36.21 | 2.48 | 1 |
| 38.26 | 2.35 | 1 |
| 39.47 | 2.28 | 1 |
| 39.98 | 2.25 | 1 |

TABLE 2

X-ray powder reflections and intensities (standardized) of ethyl 3-[(2-{[4-(hexyloxycarbonylaminoiminomethyl)phenylamino]methyl}-1-methyl-1H-benzimidazole-5-carbonyl)pyridin-2-ylamino]propionate methanesulfonate (form II)

| 2Θ [°] | $d_{hkl}$ value [Å] | intensity [%] |
|---|---|---|
| 4.3 | 20.4 | 100 |
| 8.72 | 10.1 | 3 |
| 9.68 | 9.13 | 1 |
| 11.15 | 7.93 | 1 |
| 12.42 | 7.12 | 2 |
| 13.59 | 6.51 | 1 |
| 13.95 | 6.34 | 1 |
| 15.11 | 5.86 | 1 |
| 15.97 | 5.55 | 1 |
| 16.52 | 5.36 | 1 |
| 17.45 | 5.08 | 1 |
| 17.86 | 4.96 | 2 |
| 18.45 | 4.81 | 1 |
| 19.22 | 4.61 | 2 |
| 19.89 | 4.46 | 2 |
| 21.46 | 4.14 | 2 |
| 21.98 | 4.04 | 1 |
| 22.48 | 3.95 | 1 |
| 23.75 | 3.74 | 1 |
| 25.29 | 3.52 | 1 |
| 28.17 | 3.17 | 1 |
| 28.59 | 3.12 | 1 |

TABLE 3

X-ray powder reflections and intensities (standardized) of ethyl 3-[(2-{[4-(hexyloxycarbonylaminoiminomethyl)phenylamino]methyl}-1-methyl-1H-benzimidazole-5-carbonyl)pyridin-2-ylamino]propionate methanesulfonate (hemihydrate)

| 2Θ [°] | $d_{hkl}$ value [Å] | intensity [%] |
|---|---|---|
| 3.9 | 22.8 | 100 |
| 4.4 | 20.1 | 10 |
| 5.64 | 15.7 | 2 |
| 7.57 | 11.8 | 16 |
| 8.25 | 10.7 | 17 |
| 8.77 | 10.1 | 12 |
| 9.34 | 9.46 | 7 |
| 10.69 | 8.27 | 13 |
| 11.33 | 7.80 | 3 |
| 11.66 | 7.58 | 1 |
| 11.96 | 7.39 | 1 |
| 13.04 | 6.78 | 3 |
| 14.54 | 6.09 | 11 |
| 15.16 | 5.84 | 1 |
| 16.56 | 5.35 | 13 |
| 17.27 | 5.13 | 6 |
| 17.78 | 4.98 | 12 |
| 18.75 | 4.73 | 1 |
| 19.41 | 4.57 | 3 |
| 19.95 | 4.45 | 24 |
| 20.38 | 4.35 | 4 |
| 20.84 | 4.26 | 4 |
| 21.21 | 4.19 | 12 |
| 22.22 | 4.00 | 6 |
| 22.46 | 3.96 | 5 |
| 23.05 | 3.85 | 3 |
| 23.40 | 3.80 | 4 |
| 23.85 | 3.73 | 12 |
| 24.44 | 3.64 | 7 |
| 25.30 | 3.52 | 1 |
| 25.63 | 3.47 | 1 |
| 26.22 | 3.40 | 2 |
| 26.52 | 3.36 | 3 |
| 27.06 | 3.29 | 1 |
| 27.45 | 3.25 | 2 |
| 29.27 | 3.05 | 3 |
| 30.78 | 2.90 | 2 |
| 32.32 | 2.77 | 2 |

TABLE 3-continued

X-ray powder reflections and intensities (standardized) of ethyl
3-[(2-{[4-(hexyloxycarbonylaminoiminomethyl)phenylamino]methyl}-
1-methyl-1H-benzimidazole-5-carbonyl)pyridin-2-ylamino]propionate
methanesulfonate (hemihydrate)

| 2Θ [°] | $d_{hkl}$ value [Å] | intensity [%] |
|---|---|---|
| 32.59 | 2.75 | 2 |
| 34.31 | 2.61 | 1 |
| 34.91 | 2.57 | 1 |
| 36.04 | 2.49 | 1 |
| 37.00 | 2.43 | 1 |
| 37.84 | 2.38 | 1 |
| 38.13 | 2.36 | 1 |

In the preceding Tables 1 to 3, the value "2Θ[°]" denotes the angle of diffraction in degrees and the value "$d_{hkl}$[Å]" denotes the specified distances in Å between the lattice planes.

The X-ray powder diagrams were recorded, within the scope of the present invention, using a Bruker D8 Advanced diffractometer fitted with a location-sensitive detector (OED) and a Cu anode as the X-ray source (CuK$_{\alpha 1}$ radiation, λ=1.5406 Å, 40 kV, 40 mA).

The hydrate of the compound ethyl 3-[(2-{[4-(hexyloxycarbonylaminoiminomethyl)phenyl-amino]methyl}-1-methyl-1H-benzimidazole-5-carbonyl)pyridin-2-ylamino]propionate methanesulfonate according to the invention occurs in the form of the hemihydrate under standard conditions, from which water escapes at a temperature of about 120° C., parallel to the melting of this form.

Figure 2:
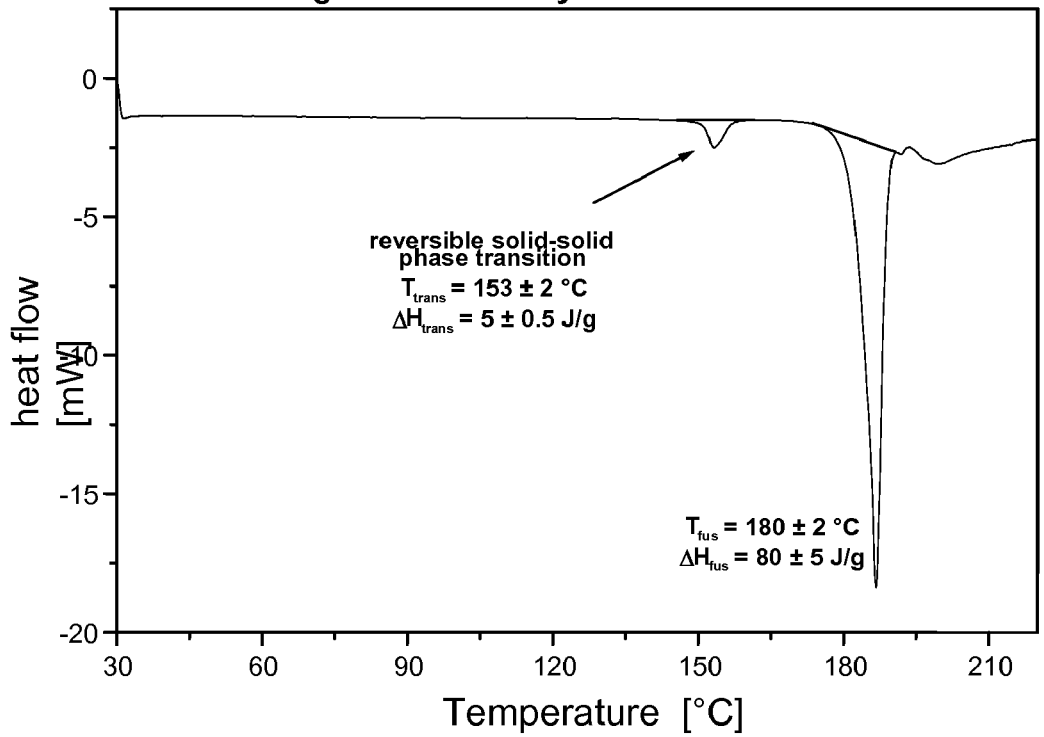
FIG. 2 shows the thermoanalysis and measurement of the melting point (DSC) for the three crystalline forms of ethyl 3-[(2-{[4-(hexyloxycarbonylaminoiminomethyl)phenylamino]-methyl}-1-methyl-1H-benzimidazole-5-carbonyl)pyridin-2-ylamino]propionate methanesulfonate.
Figure 2:
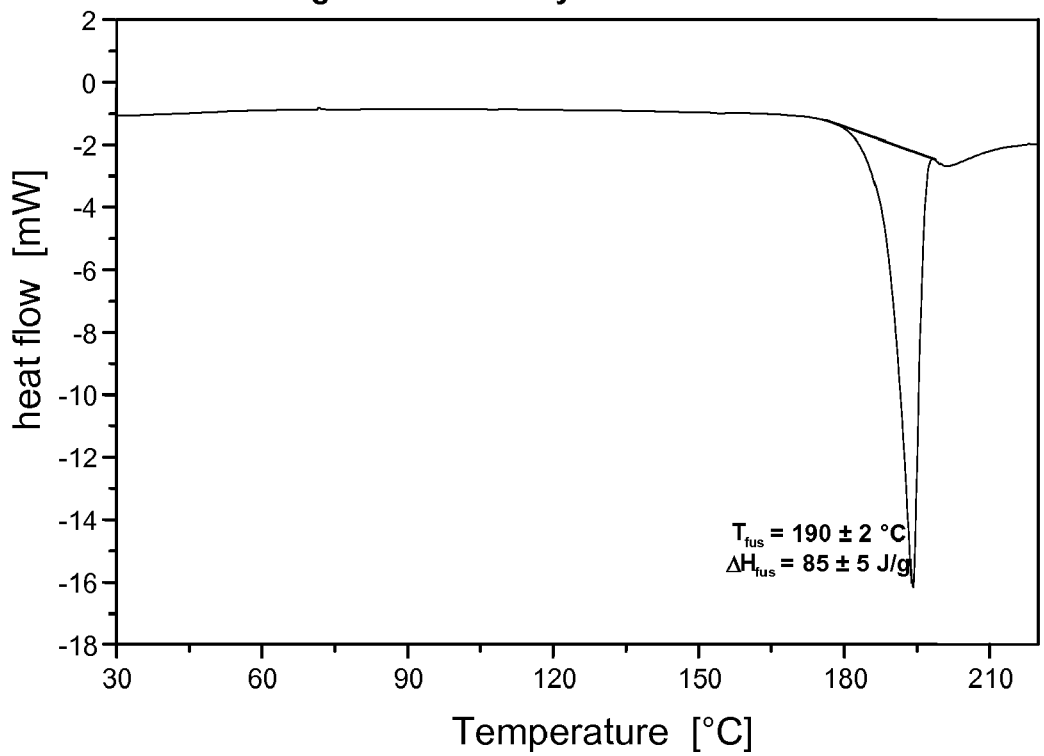
Figure 2:
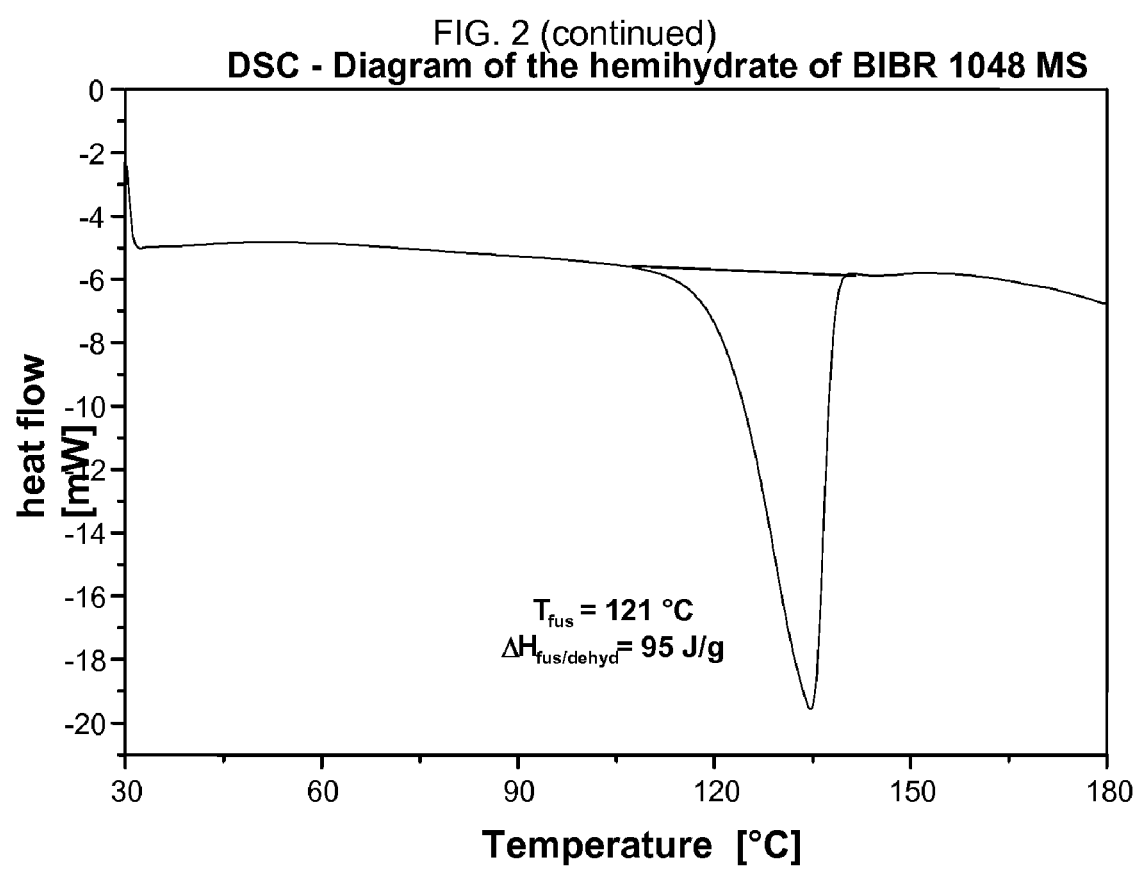

FIG. 2 shows the thermoanalysis of the three forms.

EXPERIMENTAL SECTION

Example 1

Ethyl 3-[(2-{[4-(hexyloxycarbonylaminoiminomethyl)phenylamino]methyl}-1-methyl-1H-benzimidazole-5-carbonyl)pyridin-2-ylamino]propionate methanesulfonate form I (BIBR 1048 MS polymorph I)

52.6 kg of ethyl 3-[(2-{[4-(hexyloxycarbonylaminoiminomethyl)phenylamino]methyl}-1-methyl-1H-benzimidazole-5-carbonyl)pyridin-2-ylamino]propionate base (which has preferably been purified beforehand by recrystallization from ethyl acetate) is placed in an agitator apparatus which has been rendered inert and then 293 kg of acetone is added. The contents of the apparatus are heated to 40° C. to 46° C. with stirring. After a clear solution has formed, the contents of the apparatus is filtered into a second agitator apparatus through a lens filter and then cooled to 30° C. to 36° C. 33 kg of acetone precooled to 0° C. to 5° C., 7.9 kg of 99.5% methanesulfonic acid, and for rinsing another 9 kg of acetone are placed in the suspended container of the second apparatus. The contents of the suspended container are added in metered amounts to the solution of ethyl 3-[(2-{[4-(hexyloxycarbonylaminoiminomethyl)phenylamino]methyl}-1-methyl-1H-benzimidazole-5-carbonyl)pyridin-2-ylamino]propionate base at 26° C. to 36° C. within 15 to 40 minutes. Then the mixture is stirred for 40 to 60 minutes at 26° C. to 33° C. It is then cooled to 17° C. to 23° C. and stirred for a further 40 to 80 minutes. The crystal suspension is filtered through a filter dryer and washed with a total of 270 L of acetone. The product is dried in vacuo at a maximum of 50° C. for at least 4 hours. Yield: 54.5-59.4 kg; 90%-98% of theory based on ethyl 3-[(2-{[4-(hexyloxycarbonylaminoiminomethyl)phenylamino]methyl}-1-methyl-1H-benzimidazole-5-carbonyl)pyridin-2-ylamino]propionate base Example 2

BIBR 1048 MS Polymorph II by Conversion from BIBR 1048 MS Polymorph I 4 g of BIBR 1048 MS polymorph I and 35 mL of acetone are placed in a glass flask with stirrer and reflux condenser. The suspension is heated to 45° C. to 50° C. with stirring and kept at this temperature for 4 hours. It is then cooled to 15° C. and the crystals are suction filtered through a Büchner funnel, washed with 20 mL of acetone, and dried in vacuo at 45° C.

This synthesis may also be carried out by inoculating with BIBR 1048 MS polymorph II. If the speed of conversion is low, it may be accelerated by the addition of a small amount of BIBR 1048 base (for example, on an industrial scale, about 50 g of BIBR 1048 base to roughly 90 kg of BIBR 1048 MS polymorph I) in addition to the inoculation with BIBR 1048 MS polymorph II.

Example 3

Ethyl 3-[(2-{[4-(hexyloxyvcarbonylaminoiminomethyl)phenylamino]methyl}-1-methyl-1H-benzimidazole-5-carbonyl)pyridin-2-ylamino]propionate methanesulfonate form II (BIBR 1048 MS polymorph II)

52.6 kg of ethyl 3-[(2-{[4-(hexyloxycarbonylaminoiminomethyl)phenylamino]methyl}-1-methyl-1H-benzimidazole-5-carbonyl)pyridin-2-ylamino]propionate base (which has preferably been purified beforehand by recrystallization from ethyl acetate) is placed in an agitator apparatus which has been rendered inert and then 293 kg of acetone is added. The contents of the apparatus are heated to 40° C. to 46° C. with stirring. After a clear solution has formed, the contents of the apparatus are filtered into a second agitator apparatus through a lens filter. 33 kg of acetone precooled to 0° C. to 5° C., 7.9 kg of 99.5% methanesulfonic acid, and for rinsing another 9 kg of acetone are placed in the suspended container of the second apparatus. The contents of the suspended container are added in metered amounts to the solution of ethyl 3-[(2-{[4-(hexyloxycarbonylaminoiminomethyl)phenylamino]methyl}-1-methyl-1H-benzimidazole-5-carbonyl)pyridin-2-ylamino]propionate base at 40° C. to 46° C. within 15 to 40 minutes and inoculated with 10 g of BIBR 1048 MS polymorph II (prepared according to Examples 2, for example). Then the mixture is stirred for 40 to 60 minutes at 40° C. to 46° C. It is then cooled to 17° C. to 23° C. and stirred for a further 40 to 80 minutes. The crystal suspension is filtered through a filter dryer and washed with a total of 270 L of acetone. The product is dried in vacuo at a maximum of 50° C. for at least 4 hours. Yield: 54.5-59.4 kg; 90%-98% of theory based on ethyl 3-[(2-{[4-(hexyloxycarbonylaminoiminomethyl)phenylamino]methyl}-1-methyl-1H-benzimidazole-5-carbonyl)pyridin-2-ylamino]propionate base This synthesis may also be carried out without inoculation with BIBR 1048 MS polymorph II. However, the method using inoculation is preferred.

Example 4

BIBR 1048 MS Polymorph II by Conversion from BIBR 1048 MS Polymorph I 30.7 kg of BIBR 1048 MS polymorph I is placed in an agitator apparatus which has been rendered inert and then 199 kg of acetone is added. The contents of the apparatus are inoculated with 10 g of BIBR 1048 MS polymorph II (e.g., prepared according to Example 2), heated to 40° C. to 46° C. with stirring, and kept at this temperature for at least 1 hour. Then the mixture is cooled to 17° C. to 23° C. and stirred for at least a further 40 to 80 minutes. The crystal suspension is separated off using a horizontal centrifuge and washed with a total of 45 kg of acetone. The product is dried in a vacuum drying cupboard at a maximum temperature of 50° C. for at least 4 hours. Yield: 27.7-30.1 kg; 90%-98% of theory).

This synthesis may also be carried out without inoculation with BIBR 1048 MS polymorph II. However, the method using inoculation is preferred. If the speed of conversion is low, a small amount of BIBR 1048 base (for example, about 50 g of BIBR 1048 base to roughly 90 kg of BIBR 1048 MS polymorph I) may be added, in addition to the inoculation with BIBR 1048 MS polymorph II.

Example 5

Ethyl 3-[(2-{[4-(hexyloxycarbonylaminoiminomethyl)phenylamino]methyl}-1-methyl-1H-benzimidazole-5-carbonyl)pyridin-2-ylamino]propionate methanesulfonate hemihydrate A solution of 1.53 g (15.93 mmol) of methanesulfonic acid in 15 mL of ethyl acetate was added dropwise to a solution of 10.0 g (15.93 mmol) of ethyl 3-[(2-{[4-(hexyloxycarbonylaminoiminomethyl)phenylamino]methyl}-1-methyl-1H-benzimidazole-5-carbonyl)pyridin-2-ylamino]propionate base (prepared as described in WO 98/37075) in 16.5 mL of 90% aqueous ethanol and 40 mL of ethyl acetate, with stirring, at 35° C. to 40° C. After a few minutes, the product began to crystallize out and was diluted with 30 mL of ethyl acetate. It was stirred for another 30 minutes at 35° C. to 40° C. and for a further 30 minutes at ambient (room) temperature, then the precipitate was suction filtered, washed with approximately 20 mL of ethyl acetate, and dried at 40° C. in the circulating air drying cupboard.

Yield: 99% of theory.

We claim:

1. A polymorph form II of ethyl 3-[(2-{[4-(hexyloxycarbonylaminoiminomethyl) phenylamino]-methyl}-1-methyl-1H-benzimidazole-5-carbonyl)pyridin-2-ylamino]propionate methanesulfonate, wherein the polymorph has a melting point of $T_{mp}=190°$ C.$\pm 3°$ C., determined by DSC, evaluation by peak maximum, at a heating rate of 10° C/min and possesses an X-ray powder diffraction pattern which comprises characteristic peaks as expressed in FIG. 1 (form II).

2. A pharmaceutical composition comprising:
   (a) ethyl 3-[(2-{[4-(hexyloxycarbonylaminoiminomethyl) phenylamino]methyl }-1-methyl-1H-benzimidazole-5-carbonyl)pyridin-2-ylamino]propionate methanesulfonate according to claim 1; and
   (b) one or more inert carriers and/or diluents.

* * * * *